United States Patent [19]

Hausser

[11] Patent Number: 5,385,555

[45] Date of Patent: Jan. 31, 1995

[54] LOCKABLE SAFETY SHIELD FOR HYPODERMIC SYRINGE

[75] Inventor: Roderick J. Hausser, Verona, N.J.

[73] Assignee: Becton, Dickinson and Company, Franklin Lakes, N.J.

[21] Appl. No.: 1,888

[22] Filed: Jan. 8, 1993

[51] Int. Cl.$^6$ ............................................. A61M 5/32
[52] U.S. Cl. ............................... 604/192; 604/198; 604/110
[58] Field of Search ............... 604/192, 197, 198, 187, 604/263, 110, 239-243, 181

[56] References Cited

U.S. PATENT DOCUMENTS

| | | | |
|---|---|---|---|
| 4,737,144 | 4/1988 | Choksi | 604/198 |
| 4,743,233 | 5/1988 | Schneider | 604/192 |
| 5,024,660 | 6/1991 | McNaughton | 604/110 |
| 5,059,185 | 10/1991 | Ryan | 604/198 |
| 5,067,945 | 11/1991 | Ryan | 604/198 |
| 5,137,521 | 8/1992 | Wilkins | 604/198 |
| 5,169,392 | 12/1992 | Ranford et al. | 604/198 |
| 5,217,437 | 6/1993 | Talonn et al. | 604/198 |

Primary Examiner—C. Fred Rosenbaum
Assistant Examiner—V. Alexander
Attorney, Agent, or Firm—John L. Voellmicke

[57] ABSTRACT

A lockable safety shield is provided for a hypodermic syringe. The safety shield is mounted over the syringe barrel and can be telescoped into a position for protectively guarding a sharp point on the needle cannula. Oppositely facing stop surfaces on the syringe barrel and the safety shield prevent complete telescoped removal of the safety shield from the syringe barrel. A deflectable wall on the syringe barrel snaps into engagement with locking teeth on the safety shield when the safety shield has been telescoped into a position for guarding the needle cannula point to prevent exposure of the used needle cannula.

22 Claims, 5 Drawing Sheets

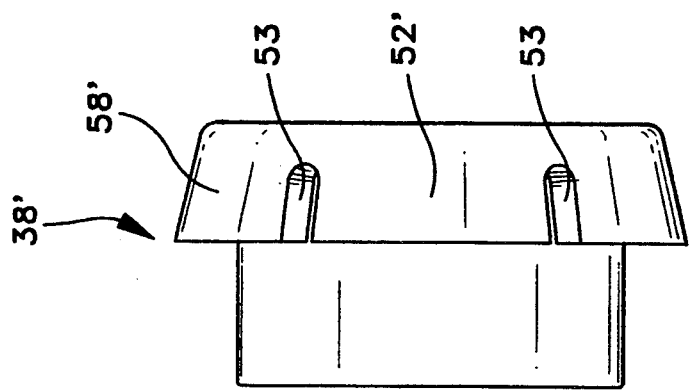
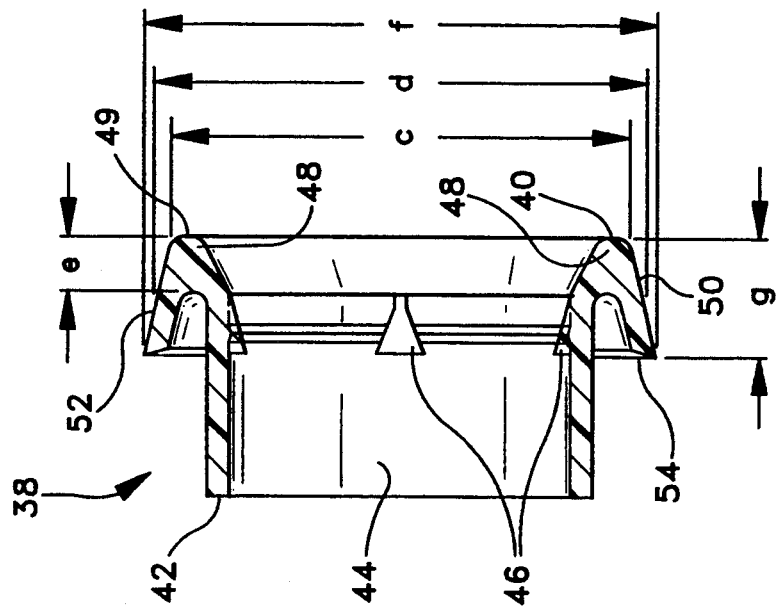
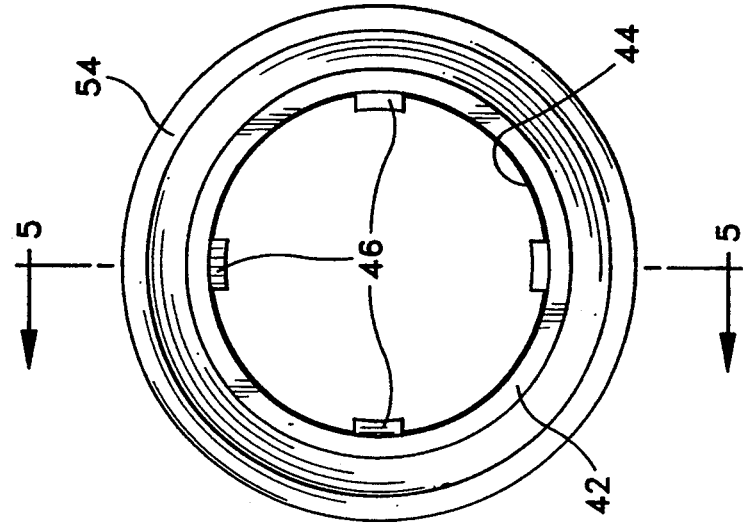

LOCKABLE SAFETY SHIELD FOR HYPODERMIC SYRINGE

BACKGROUND OF THE INVENTION

1. Field of the Invention The subject invention relates to a hypodermic syringe having a sharp needle cannula and a rigid protective shield that can be locked in a position around the needle cannula for helping to prevent accidental needle sticks.

2. Description of the Prior Art Hypodermic syringes typically have a needle shield removably mounted over the needle cannula to avoid accidental needle sticks and to prevent damage to the needle before use. The needle shield can be safely removed and discarded when the hypodermic syringe is about to be used.

Accidental needle sticks occurring after the needle cannula has been used pose a substantially greater health risk, because the used needle cannula may be contaminated. Most health care facilities include sharps receptacles into which a used hypodermic syringe may be safely deposited. However, the hypodermic syringe is not always used near a sharps receptacle, and the needs of a patient may prevent the health care worker from traveling to the sharps receptacle immediately after using the hypodermic syringe.

The prior art includes hypodermic syringes with a safety shield telescoped over the syringe barrel and moveable between a proximal position where the needle cannula is exposed and a distal position where the needle cannula is surrounded. The prior art safety shield is retained in its proximal position until after the needle cannula is used. The safety shield then is moved distally on the syringe barrel to protectively enclose the needle cannula for preventing accidental needle sticks.

The prior art includes many structures for retaining the safety shield in its distal position after using the hypodermic syringe. For example, some prior art hypodermic syringes include an annular rib on the safety shield that can be engaged in an annular groove on the syringe barrel, as shown, for example, in U.S. Pat. No. 5,067,945.

The prior art also includes hypodermic syringes with bayonet-type interengagements between the safety shield and the syringe barrel which require both an axial movement and a twisting movement to retain the safety shield in either its proximal position or its distal position. A prior art hypodermic syringe with such a bayonet-type connection is shown in U.S. Pat. No. 5,024,660.

Other prior art hypodermic syringes rely upon a threaded interengagement between the safety shield and the syringe barrel, as shown in U.S. Pat. No. 4,743,233.

U.S. Pat. No. 5,059,185 teaches a safety shield with slots extending into the proximal end to define deflectable fingers which are configured to engage a continuous annular groove in an outer surface of the syringe barrel.

Other prior art hypodermic syringes form either the needle guard or the syringe barrel with a discontinuous wall that defines at least one deflectable finger intermediate the length of the needle guard. A locking detent at the end of the deflectable finger is engageable in an opposed groove. Hypodermic syringes of this general design are shown in U.S. Pat. No. 5,137,521 to Wilkens or U.S. Pat. No. 4,737,144 to Choksi. Additionally the prior art safety shields do not provide adequate locking of the needle guard in its distal position for protecting against re-exposure of the needle cannula. Furthermore, many of the prior art designs do not provide adequate tactile and audible indication of the safety shield being locked in its distal position for protectively surrounding the needle cannula.

Many of the prior art designs are very sensitive to dimensional tolerances, and hence are complex and costly to manufacture. Some prior art designs allow the safety shield to be extended to its most distal needle covering position while not being locked so that the device appears to be safe when it is not. Other prior art devices lock automatically upon extension, however, the user may not be sure that the needle guard is locked unless there is an audible, visual and/or tactile indication that such locking has occurred. Accordingly, although the prior art has addressed syringes having self-contained safety shields which can be locked to help prevent accidental needle sticks there is still a need for a simple, straight-forward, reliable, easily fabricated syringe with a locking safety shield having a locking structure which is less tolerance dependent while providing adequate locking force to hold the safety shield in the locked position.

SUMMARY OF THE INVENTION

The subject invention is directed to a hypodermic syringe having a sharp needle cannula and a rigid safety shield. The safety shield is telescoped over the syringe barrel, and may be slid from a proximal retracted position, where the needle cannula is exposed, to a distal position where the needle cannula is substantially surrounded by the safety shield.

The safety shield and the the hypodermic syringe comprise stop means for preventing removal of the safety shield from the hypodermic syringe and locking means for preventing return of the safety shield from its distal position surrounding the needle cannula to its proximal retracted position. The stop means includes at least one rigid stop surface facing distally on the safety shield and at least one rigid stop surface facing proximally on the syringe barrel. The rigid stop surfaces are disposed to engage one another when the safety shield is moved sufficient in the distal direction to protectively surround the needle cannula. The rigid stop surface of the safety shield may comprise a plurality of stop surfaces disposed on a corresponding plurality of stop blocks at the proximal end of the safety shield. The stop blocks may be dimensioned for releasably holding the safety shield in a proximal position on the syringe barrel with the needle cannula exposed for use.

The locking means comprises at least one resiliently deflectable lock wall on the syringe barrel, and dimensioned to engage at least one locking tooth on the safety shield. The resiliently deflectable lock wall is dimensioned and configured to deflect easily during the telescoped movement of the safety shield in the distal direction over the syringe barrel. However, the deflectable lock wall will resiliently return toward an undeflected condition after the safety shield protectively surrounds the needle cannula. The deflectable lock wall is configured to engage the locking tooth for preventing reverse or proximal movement of the safety shield on the syringe barrel. Preferably, the resiliently deflectable lock wall is dimensioned and configured to snap into engagement with the locking tooth to provide audible and/or tactile indication that the safety shield is in its locked condition surrounding the needle cannula.

In a preferred embodiment, the resiliently deflectable lock wall and the stop surface of the syringe barrel are oppositely facing portions of an annular locking collar mounted over the distal end of syringe barrel. In this embodiment, a plurality of rigid locking teeth may be circumferentially spaced around the safety shield. The locking teeth may be spaced distally from the stop surfaces of the safety shield by a distance sufficient to capture the locking collar between the locking teeth and the stop surfaces of the safety shield. Prior to using the hypodermic syringe, the safety shield may be frictionally retained in a proximal position on the syringe barrel. After the hypodermic syringe is used, opposed axial forces are exerted on the safety shield and on syringe barrel to enable the telescoped movement of the safety shield distally relative to the syringe barrel and the needle cannula. The locking teeth will engage the resiliently deflectable lock wall of the locking collar, and will cause this portion of the locking collar to resiliently deflect inwardly. After sufficient distal movement of the safety shield, the locking teeth will clear the lock wall of the locking collar, thereby enabling the lock wall to resiliently return toward an undeflected condition. Proximally directed forces on the safety shield will be resisted by the deflectable lock wall of the locking collar. Conversely, distally directed forces on the safety shield will cause the stop blocks of the safety shield engage the stop surface on the locking collar to prevent complete removal of the safety shield from the syringe barrel.

The locking teeth and the cooperating resiliently deflectable lock wall of the subject invention offer several distinct advantages. First, the forces required to positively lock the safety shield relative to syringe barrel can be very low in view of the easy one-way deflectability of the lock wall. However, the unlocking forces can be very high, particularly when compared to the low locking forces. Thus, a hypodermic syringe can be provided that is easy to lock in a safe position, but very difficult or impossible to unlock. Second, dimensional tolerances for the safety shield and the syringe barrel telescoped therewith are substantially less critical, thereby reducing manufacturing costs and providing lower reject rates.

BRIEF DESCRIPTION OF THE DRAWINGS

FIG. 4 is an end elevational view of a locking collar;

FIG. 5 is a cross-sectional view taken along line 5—5 in FIG. 4;

FIG. 6 is a side elevational view showing an alternate locking collar;

DETAILED DESCRIPTION OF THE PREFERRED EMBODIMENT

Figure 1:
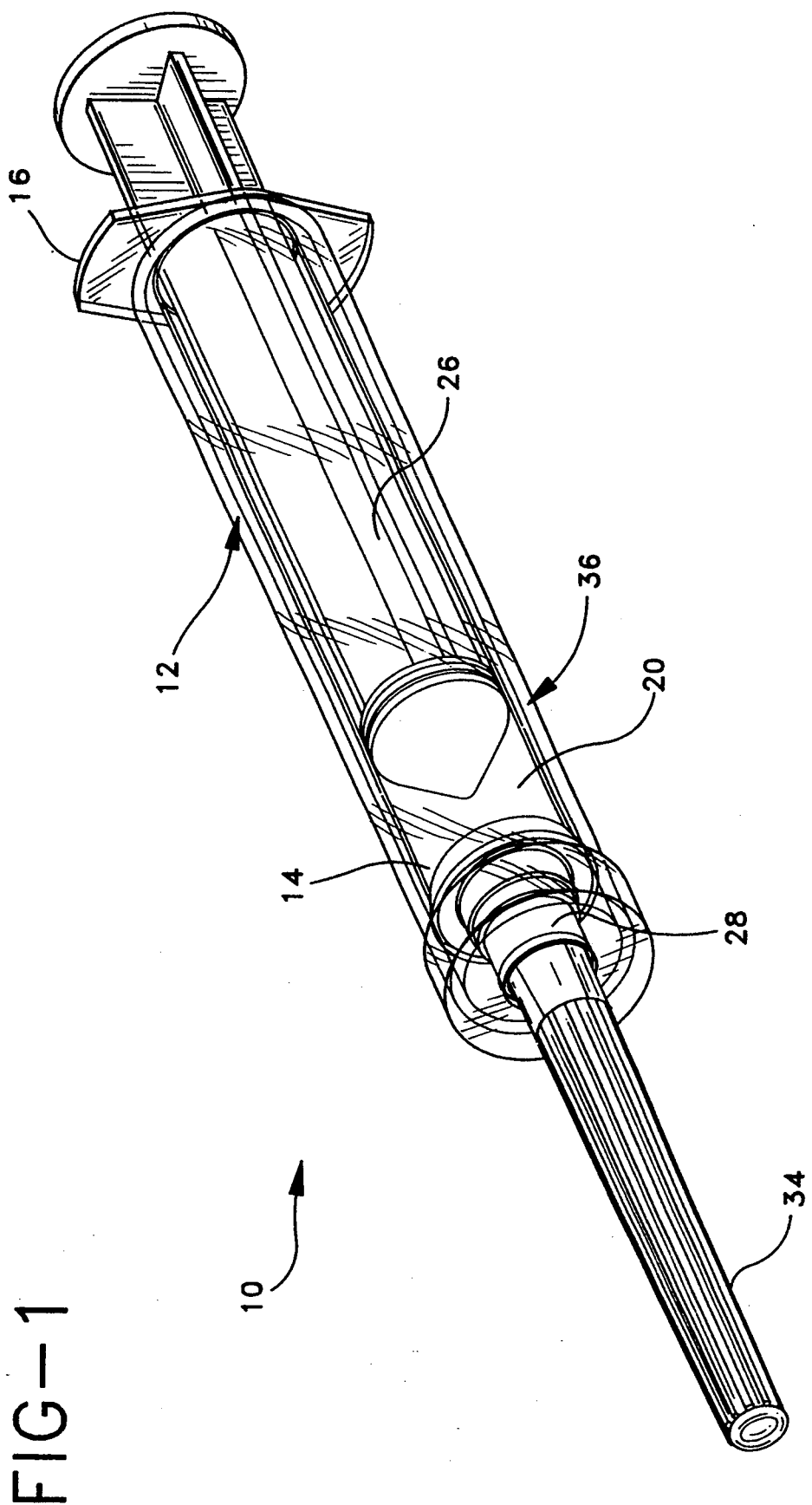
FIG. 1 is a perspective view of a hypodermic syringe incorporating a safety shield in accordance with the subject invention.
Figure 2:
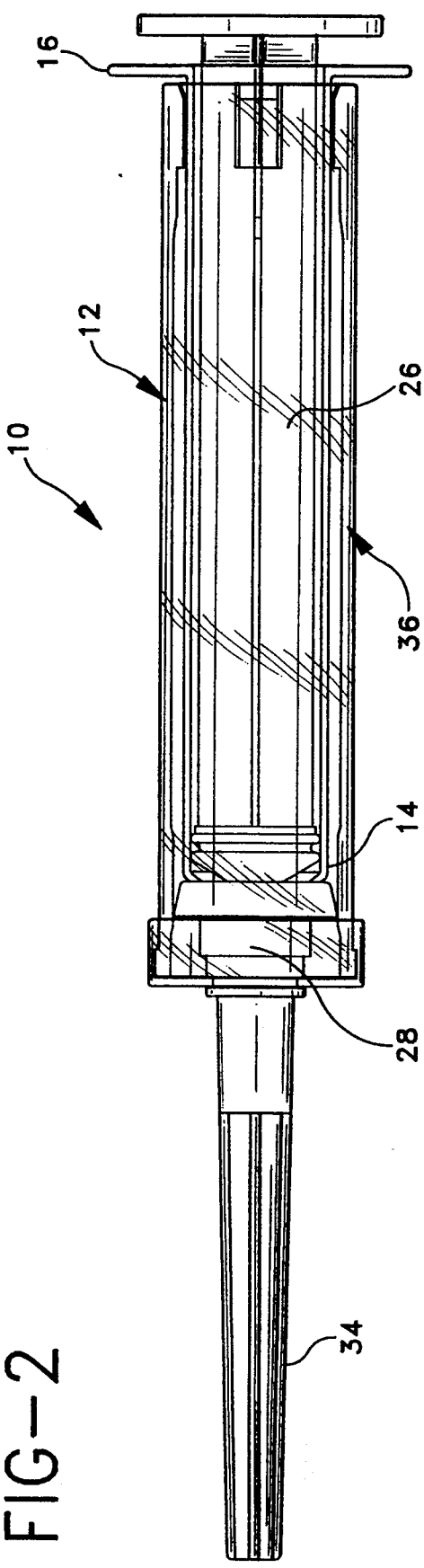
FIG. 2 is a side elevational view of the hypodermic syringe and safety shield depicted in FIG. 1.
Figure 3:
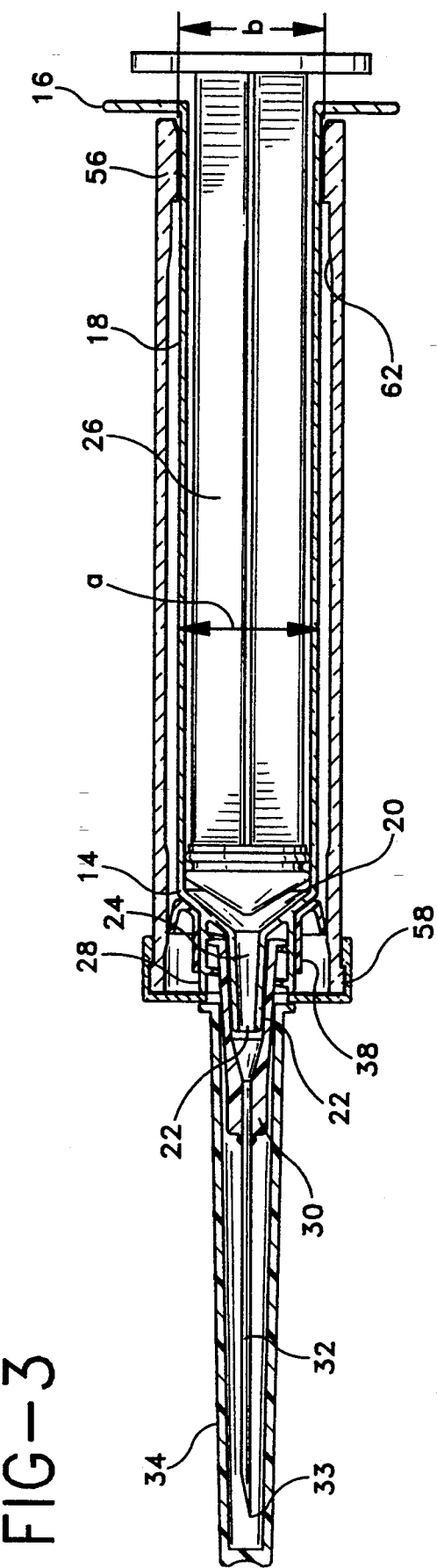
FIG. 3 is a cross-sectional view taken along line 3—3 in FIG. 2.

A hypodermic syringe in accordance with the invention is identified generally by the numeral 10 in FIGS. 1–3. Hypodermic syringe 10 includes a generally cylindrical syringe barrel 12 having a distal end 14, an open proximal end 16 and a generally cylindrical wall 18 extending therebetween to define a fluid receiving chamber 20. Cylindrical wall 18 of syringe barrel 12 defines an outside diameter "a" along most of its length, as shown in FIG. 3. However, the outside diameter of syringe barrel 12 is larger near proximal end 16, as indicated by dimension "b". With further reference to FIG. 3, the distal end of syringe barrel 12 is characterized by a tip 22 having a fluid passage 24 extending therethrough and communicating with chamber 20. A plunger 26 is disposed in sliding fluid-tight engagement with cylindrical wall 18 of syringe barrel 12. Sliding movement of plunger 26 toward distal end 14 causes fluid in chamber 20 to be expelled through passage 24. Conversely, sliding movement of plunger 26 away from distal end 16 of syringe barrel 12 will draw fluid through passage 24 and into chamber 20.

The distal end of syringe barrel 12 is further characterized by a locking luer-type collar 28 disposed in spaced concentric relationship around tip 22. Luer collar 28 includes an array of internal threads to enable threaded mounting of a needle hub 30 between collar 28 and tip 22. A needle cannula 32 is securely mounted to needle hub 30 and is in fluid communication with passage 24 and chamber 20.

Needle cannula 32 includes sharp tip 33. To prevent accidental needle sticks prior to use of hypodermic syringe 10, a needle shield 34 is removably mounted over needle cannula 32. Needle shield 34 can be removed from hypodermic syringe 10 immediately prior to use to substantially reduce the potential for accidental needle sticks prior to using the hypodermic syringe. However, as noted above, the potential for disease transmission from an accidental needle stick is greater after the hypodermic syringe 10 has been used.

A safety shield 36 and a locking collar 38 are provided to avoid needle sticks after using hypodermic syringe 10. As shown most clearly in FIGS. 3–5, locking collar 38 is a generally annular structure unitarily formed from a thermoplastic material and having opposed proximal and distal ends 40 and 42 respectively. An inner surface 44 extends between ends 40 and 42 and is dimensioned to tightly engage outer surface of luer collar 28 at distal end 14 of syringe barrel 12. As shown most clearly in FIG. 5, inner surface 44 of locking collar 38 is preferably characterized by a plurality of spaced apart barbs 46 pointing inwardly and in a generally distal direction. The barbs enable locking collar 38 to be slid in a distal to proximal direction over distal end 14 of syringe barrel 12. However barbs 46 bite into the thermoplastic material of luer collar 28 to prevent removal of locking collar 38 from syringe barrel 12 in a proximal-to-distal direction.

Locking collar 38 is characterized by a solid annular stop wall 48 extending distally from proximal end 40. Stop wall 48 includes an outer circumferential surface which expands frustoconically outwardly at locations distally of proximal end 40 of locking collar 38. Thus, the proximal end 40 defines a minor outside diameter "c", as shown in FIG. 5, and a major outside diameter "d". Minor outside diameter "c" at proximal end 40 of locking collar 38 exceeds outside diameter "a" of cylindrical wall 18 of syringe barrel 12. Thus, proximal end 40 extends radially outwardly beyond syringe barrel 12 as shown in FIG. 3. Solid annular stop wall 48 defines an axial length "e" which is selected to resist distally directed forces exerted on locking collar 38 by safety shield 36 as explained further herein. More particularly, the axial length of stop wall 48 and the frustoconical shape of outer surface 50 will cause distally directed forces on locking collar 38 to urge locking collar 38 radially inwardly such that barbs 46 bite deeper into luer collar 28 at distal end 14 of syringe barrel 12.

Locking collar 38 further includes a resiliently deflectable lock wall 52 projecting distally and outwardly from stop wall 48 to define a major outside diameter "f" for locking collar 38. More particularly, resiliently deflectable lock wall 52 is spaced radially outwardly from portions of locking collar 38 disposed distally of annular stop wall 48 to enable radially inward deflection of lock wall 52. The resiliently deflectable lock wall is preferably a substantially continuous conical wall as shown in FIGS. 4 and 5. Alternatively, as shown in FIG. 6, a locking collar 38' can be provided with a plurality of independently deflectable lock walls 52' separated from one another by slits 53. Each independently deflectable lock wall 52' defines an arc segment of a cone. The segmentation of the deflectable lock wall avoids hoop stress and facilitates inward deflection of lock walls 52'.

Returning to FIG. 5, resiliently deflectable lock wall 52 includes a distal end 54 of generally concave frustoconical shape defining an angle of about 30° to a radius of locking collar 38. The concave configuration of distal end 54 functions as a ramp which urges deflectable lock wall 52 radially outwardly in response to distal-to-proximal forces exerted thereon.

Safety shield 36 is an elongate tubular structure disposed in sliding telescoped relationship over syringe barrel 12. Safety shield 36 is molded from thermoplastic material to include opposed distal and proximal ends 58 and 56 respectively, and an axial length greater than The length of needle cannula 32. The safety shield preferably includes an inner circumferential surface 60 having a plurality of longitudinally extending ribs 62 which preferably define an inside diameter slightly less than the outer diameter f at the distal end of deflectable lock wall 52 of locking collar 38. Thus, safety shield 36 will remain substantially centered on syringe barrel 12 by sliding cooperation between ribs 62 and locking collar 38.

Proximal end 56 of safety shield 36 is characterized by a plurality of spaced apart stop blocks 64. Each stop block 64 includes an inwardly facing holding surface 66 aligned substantially parallel to the axis of safety shield 36 and a radially aligned, distally facing stop surface 68. Inwardly facing holding surfaces 66 of stop blocks 64 define an inside diameter "h" is preferably approximately equal to or slightly less than the outside diameter "b" of syringe barrel 12 at locations adjacent proximal end 16 thereof. Thus, safety shield 36 can be frictionally held in a proximal position on syringe barrel 12 by holding surfaces 66 of stop blocks 64. The inside diameter "h" defined by stop blocks 64 is less than the outer diameter "c" at proximal end 40 of locking collar 38. Thus, distally directed telescoped movement of safety shield 36 along syringe barrel 12 is positively limited by proximal end 40 of locking collar 38. In particular, the radially aligned distally facing stop surfaces 68 of stop blocks 64 will positively engage annular proximally facing end surface 49 of locking collar 38 to prevent proximal-to-distal removal of safety shield 36 from syringe barrel 12.

Figure 9:
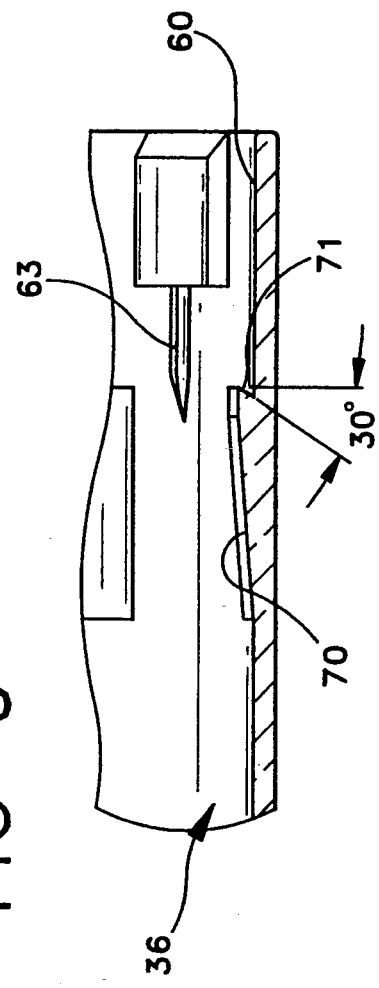
FIG. 9 is a cross-sectional view taken along line 9—9 in FIG. 8.

Safety shield 36 is further characterized by a plurality of spaced apart locking teeth 70 which are disposed distally of stop blocks 64 by a distance "i" which is greater than distance "g" between stop surface 49 and the distal end of resilient lock wall 52 on locking collar 38. Locking teeth 70 are ramped to define a minor inside diameter "l" at locations closer to proximal end 56 of safety shield 36. Minor inside diameter "l" is less than major diameter "f" defined by resilient deflectable lock wall 52 of locking collar 38. Locking teeth 70 include proximal ends 71 which are aligned to a radius at an angle approximately equal to the angle of frustoconical surface 54 at the extreme distal end of resilient deflectable lock 52 which in this preferred embodiment is approximately 30° as illustrated in FIG. 9.

Hypodermic syringe 10 is assembled by first sliding safety shield 36 over syringe barrel 12. Locking collar 38 then is slid onto syringe barrel 12, in a distal-to-proximal direction, such that barbs 46 bite into luer collar 28 to prevent subsequent proximal-to-distal removal of locking collar 38.

As noted above, safety shield 36 is frictionally retained in a proximal position on syringe barrel 12 until hypodermic syringe 10 is used. After use, safety shield 36 is telescoped in a distal direction over syringe barrel 12. Initial distal movement of safety shield 36 is restrained by contact between ribs 62 and surface 50 of locking wall 52, and by contact between surface 66 of stop block 64 and barrel outside diameter b. Locking teeth 70 then will engage and inwardly deflect frustoconical locking wall 52 of locking collar 38, and enable continued distal advancement of safety shield 36 over syringe barrel 12. After sufficient distal movement, locking teeth 70 will move distally beyond frustoconical deflectable locking wall 52 of locking collar 38. At this point, locking wall 52 will resiliently return toward an undeflected or less deflected condition defining an outside diameter "f" greater than the inside diameter "h" defined by locking teeth 70. As a result, re-exposure of needle cannula 32 is prevented by engagement between locking teeth 70 with the locking wall 52 of locking collar 38. The frustoconical concave configuration of distal end 54 locking wall 52 and the corresponding configuration of proximal ends 71 of locking teeth 70 will urge frustoconical locking walls 52 of locking collar 38 outwardly and tightly into safety shield 36, thereby further enhancing locking in response to proximal forces on safety shield 36. Because of surface 71 on the locking teeth and the configuration of the resiliently deflectable locking walls 52, a proximally directed force to the shield will cause the locking walls 52 to expand and more securely engage the locking teeth. Accordingly, increased force is met with increased resistance. This is an important feature of the invention. This locking engagement of teeth 70 with locking collar 38 can be accompanied by a clearly recognizable tactile and audible indication of complete locking of safety shield 36 as teeth 70 pass locking collar 38 and enable the resilient return of locking wall 52 toward an undeflected condition. Removal of safety shield 36 in a distal direction is prevented by engagement of stop blocks 64 with the stop surface defined by proximal end 40 of locking collar 38.

Figure 8:
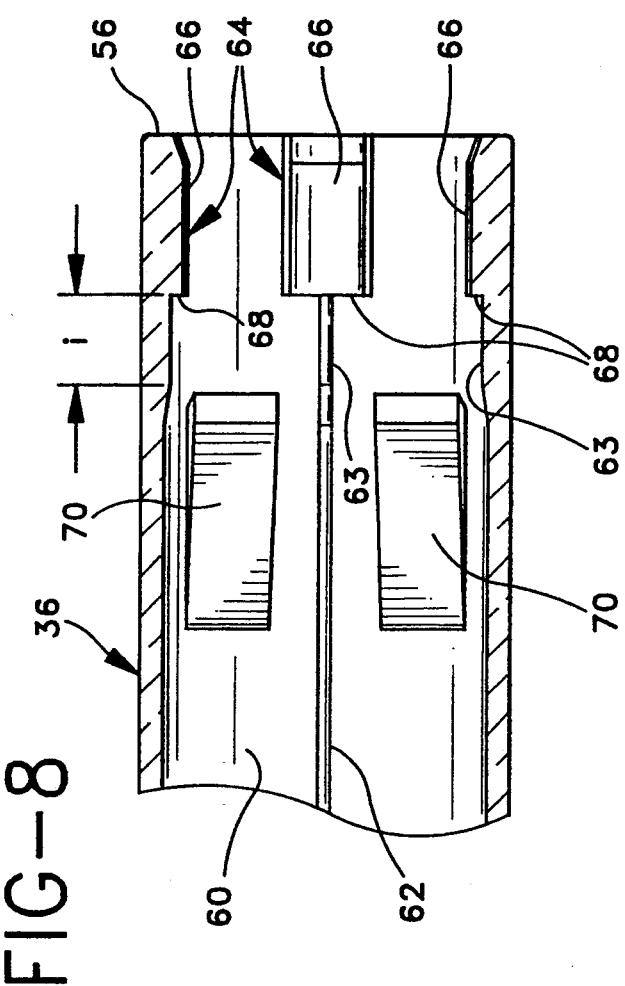
FIG. 8 is a cross-sectional view taken along line 8—8 in FIG. 7.
Figure 7:
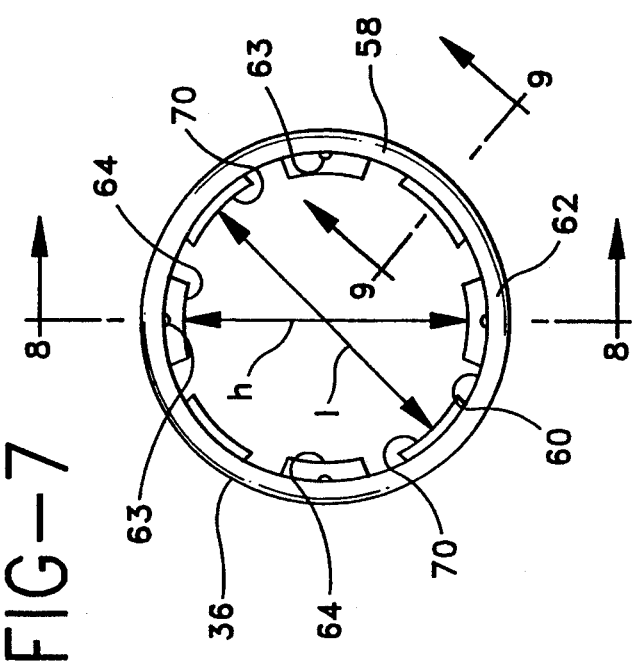
FIG. 7 is an end elevational view of a safety shield in accordance with the subject invention.
Figure 10:
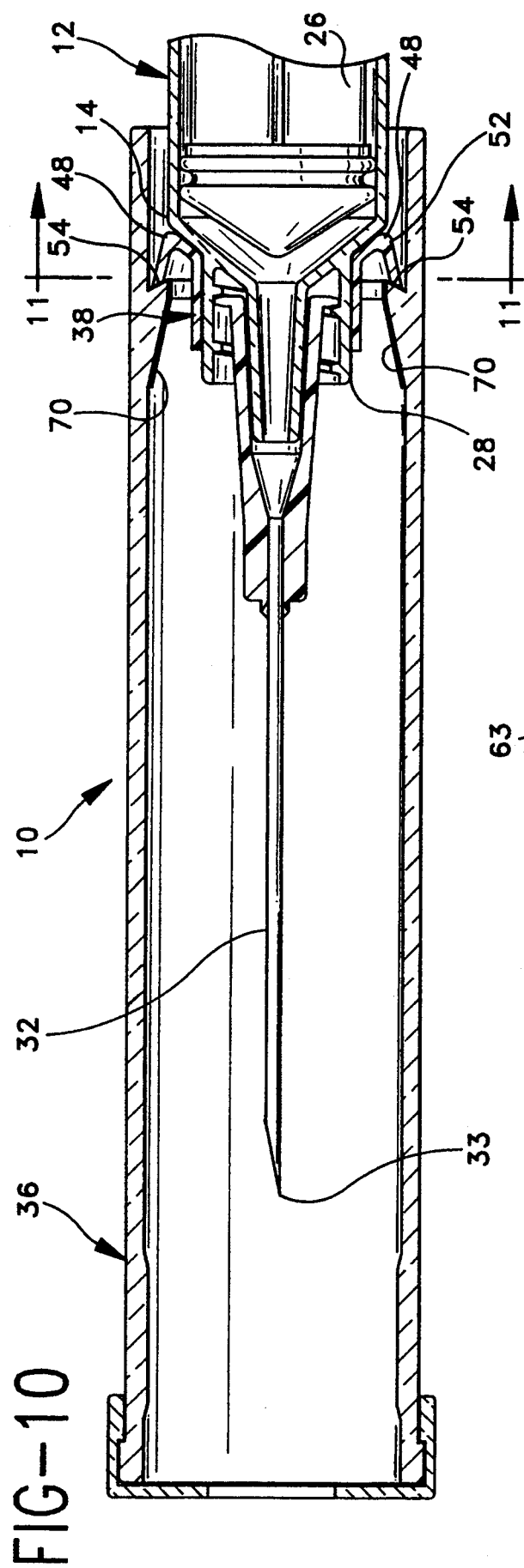
FIG. 10 is a side elevational view similar FIG. 2 but showing the safety shield partly section and in the distal locked position relative to the hypodermic syringe.
Figure 11:
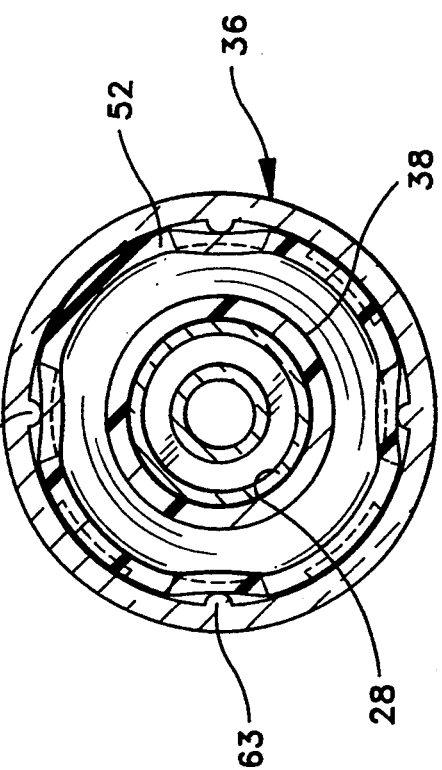
FIG. 11 is a cross-sectional view of the syringe of FIG. 10 taken along line 11—11.

Longitudinal ribs 62, as best illustrated in FIG. 8, are enlarged in the area between locking teeth 70 and stop block 64, as indicated by numeral 63. When locking collar 38 is in the extended locked position, as illustrated in FIGS. 10 and 11, rib portion 63 further enhances the locking relationship between distal end 54 of locking wall 52 and proximal ends 71 of locking teeth 70 by forcing distal end 54 of the locking wall into a non-circular shape having its largest diameter where distal end 54 engages proximal end 71 of the locking teeth.

What is claimed is:

1. A safety assembly for a hypodermic syringe having a syringe barrel with opposed proximal and distal ends, said distal end of said syringe barrel having a needle cannula mounted thereto, said safety assembly comprising:
   a locking collar for secure mounting around said syringe barrel, and having a stop wall projecting outwardly from said syringe barrel and at least one deflectable lock wall projecting distally and outwardly from said locking collar; and
   a safety shield for mounting over said syringe barrel for telescoping movement from a proximal position where said needle cannula is exposed to a locked distal position where said safety shield protectively surrounds said needle cannula, said safety shield including at least one stop block projecting inwardly therefrom said stop block being engageable with said stop wall of said locking collar for preventing removal of said safety shield from said syringe barrel, said safety shield further comprising at least one locking tooth dimensioned and disposed to generate inward deflection of said lock wall of said locking collar during said telescoping movement of said safety shield from said proximal position toward said distal position, said locking tooth being spaced distally from said stop block a sufficient distance to enable engagement of said lock wall and said stop wall of said locking collar between said locking tooth and stop block of said safety shield, and said locking tooth configured to lockably engage said deflectable lock wall to prevent proximal movement of said safety shield from its locked distal position wherein said locking engagement of said locking collar and said safety shield can be achieved solely upon axial movement of the safety shield distally with respect to said barrel.

2. A safety assembly of claim 1 wherein said locking collar includes an inner circumferential surface comprising a plurality of inwardly and distally directed barbs for biting into the syringe barrel for preventing proximal-to-distal removal of said locking collar from said syringe barrel.

3. A safety assembly as in claim 1, wherein said deflectable lock wall is a continuous frustoconically-shaped wall.

4. A safety assembly as in claim 1, wherein said deflectable lock wall of said locking collar comprises a plurality of independently deflectable spaced apart locking wall segments projecting distally and outwardly from said locking collar.

5. A safety assembly as in claim 1, wherein said deflectable lock wall of said locking collar includes a generally concavely tapered distal end for generating outward deflection of said lock wall in response to proximally directed forces exerted thereon.

6. A safety assembly as in claim 5, wherein said concavely tapered distal end of said lock wall defines a frustoconically shaped surface inclined at an angle of approximately 30° with a radius of said locking collar.

7. A safety assembly as in claim 5, wherein said locking tooth of said safety shield includes a proximal end tapered for generating outward deflection of said lock wall of said locking collar in response to proximally directed forces of said locking tooth on said deflectable lock wall.

8. A safety assembly as in claim 1, wherein said safety shield includes opposed proximal and distal ends, said at least one stop block comprises a plurality of circumferentially spaced stop blocks generally adjacent said proximal end of said safety shield, and wherein said at least one locking tooth comprises a plurality of circumferentially spaced locking teeth.

9. A safety assembly as in claim 1, wherein said locking tooth is ramped to generate inward deflection of said locking wall of said locking collar in response to distally directed telescoped movement of said safety shield from said proximal position on said syringe barrel to said locked distal position.

10. A safety assembly comprising:
    a syringe barrel with opposed proximal and distal ends, said distal end of said syringe barrel having a needle cannula mounted thereto;
    a locking collar securely mounted around said distal end of said syringe barrel and including a stop wall projecting outwardly from said syringe barrel and at least one deflectable lock wall projecting distally and outwardly from said locking collar; and
    a safety shield mounted over said syringe barrel for telescoping movement from a proximal position where said needle cannula is exposed to a locked distal position where said safety shield protectively surrounds said needle cannula, said safety shield including at least one stop block extending inwardly therefrom toward said syringe barrel, said stop block being engageable with said stop wall of said locking collar for preventing removal of said safety shield from said syringe barrel, said safety shield further comprising at least one locking tooth dimensioned and disposed to generate inward deflection of said lock wall of said locking collar during said telescoping movement of said safety shield from said proximal position toward said locked distal position, said locking tooth being spaced distally from said stop block a sufficient distance to enable engagement of said lock wall and said stop wall of said locking collar between said locking tooth and stop block of said safety shield, and said locking tooth configured to lockably engage said deflectable lock wall to prevent proximal movement of said safety shield from its locked distal position wherein said locking engagement of said locking collar and said safety shield can be achieved solely upon axial movement of the safety shield distally with respect to said barrel.

11. A safety assembly as in claim 10, wherein said locking collar includes an inner circumferential surface dimensioned to tightly engage over said distal end of said syringe barrel for preventing proximal-to-distal removal of said locking collar from said syringe barrel.

12. A safety assembly of claim 10 wherein said locking collar includes an inner circumferential surface comprising a plurality of inwardly and distally directed barbs for biting into the syringe barrel for preventing proximal-to-distal removal of said locking collar from said syringe barrel.

13. A safety assembly as in claim 10, wherein said deflectable lock wall is a continuous frustoconically shaped wall.

14. A safety assembly as in claim 13 wherein said at least one locking tooth comprises a plurality of circumferentially spaced locking teeth.

15. A safety assembly as in claim 14 wherein said locking collar includes a plurality of inwardly projecting, longitudinally·oriented, circumferentially spaced ribs at its proximal end, said ribs being positioned between said plurality of circumferentially spaced locking teeth, said ribs being sized to define a diameter which is less than the outsider diameter defined by said deflectable locking wall so that when said safety shield is in said locked distal position said ribs force said deflectable locking wall into a non-circular shape having its largest diameter where said deflectable locking wall engages said locking teeth.

16. A safety assembly as in claim 10, wherein said deflectable lock wall of said locking collar comprises a plurality of independently deflectable spaced apart lock wall segments projecting distally and outwardly from said locking collar.

17. A safety assembly as in claim 10, wherein said deflectable lock wall of said locking collar includes a generally concavely tapered distal end for generating outward deflection of said lock wall in response to proximally directed forces exerted thereon.

18. A safety assembly as in claim 17, wherein said concavely tapered distal end of said locking wall defines a frustoconically shaped surface inclined at an angle of approximately 30° with a radius of said locking collar.

19. A safety assembly as in claim 17, wherein said locking tooth of said safety shield includes a proximal end tapered for generating outward deflection of said lock wall of said locking collar in response to proximally directed forces of said locking tooth on said deflectable lock wall.

20. A safety assembly as in claim 10, wherein said safety shield includes opposed proximal and distal ends, said at least one stop block comprises a plurality of circumferentially spaced stop blocks generally adjacent said proximal end of said safety shield, and wherein said at least one locking tooth comprises a plurality of circumferentially spaced locking teeth.

21. A safety assembly as in claim 10, wherein said locking tooth is ramped to generate inward deflection of said lock wall of said locking collar in response to distally directed telescoped movement of said safety shield from said proximal end of said syringe barrel to said locked distal position.

22. A safety assembly as in claim 10, wherein said syringe barrel includes an enlarged annular portion adjacent said proximal end, said stop block being frictionally engageable with said enlarged annular portion for releasably retaining said safety shield in said proximal position.

* * * * *